United States Patent [19]

Shaw et al.

[11] 4,295,470
[45] Oct. 20, 1981

[54] OPTICAL CATHETERS AND METHOD FOR MAKING SAME

[75] Inventors: Robert F. Shaw, Portola Valley; John Sperinde, San Jose, both of Calif.

[73] Assignee: Oximetrix, Inc., Mountain View, Calif.

[21] Appl. No.: 964,612

[22] Filed: Nov. 29, 1978

Related U.S. Application Data

[63] Continuation of Ser. No. 733,279, Oct. 18, 1976, abandoned.

[51] Int. Cl.³ .............................................. A61B 5/02
[52] U.S. Cl. ..................................... 128/634; 356/41
[58] Field of Search ............................... 128/633–634, 128/349 R; 250/227; 350/96.2-96.24; 362/32; 65/4 B; 356/39–42

[56] References Cited

U.S. PATENT DOCUMENTS

| | | | |
|---|---|---|---|
| 3,068,742 | 12/1962 | Hicks et al. | 128/214 R |
| 3,131,690 | 5/1964 | Innis et al. | 350/96.22 |
| 3,417,746 | 12/1968 | Moore et al. | 128/398 |
| 3,455,625 | 7/1969 | Brumley | 350/96.22 |
| 3,554,721 | 1/1971 | Gardner | 65/4 |
| 3,647,299 | 3/1972 | Lavallee | 356/39 |
| 3,771,873 | 11/1973 | Tourret | 250/227 |
| 3,847,483 | 11/1974 | Shaw et al. | 128/634 |
| 3,904,269 | 9/1975 | Lebduska et al. | 350/96.22 |
| 3,937,558 | 2/1976 | Mukai et al. | 250/227 |
| 3,937,952 | 2/1976 | Ripley et al. | 250/227 |
| 3,961,621 | 6/1976 | Northeved | 128/6 |
| 4,015,894 | 4/1977 | Rockton | 350/96.22 |

FOREIGN PATENT DOCUMENTS

| | | | |
|---|---|---|---|
| 2503835 | 8/1975 | Fed. Rep. of Germany | 128/6 |
| 1250712 | 10/1971 | United Kingdom | 250/227 |
| 1268855 | 3/1972 | United Kingdom | 250/227 |
| 1275094 | 5/1972 | United Kingdom | 250/227 |
| 1357156 | 6/1974 | United Kingdom | 350/96.22 |
| 1411877 | 10/1975 | United Kingdom | 350/96.22 |

*Primary Examiner*—Stephen C. Pellegrino
*Assistant Examiner*—Francis J. Jaworski
*Attorney, Agent, or Firm*—Lyon & Lyon

[57] ABSTRACT

Catheter apparatus having transmitting and receiving optical fibers for photometric analysis of a fluid eliminates the need for individually calibrating each catheter within a population of catheters by making substantially uniform the center-to-center spacing between the outlet aperture of each and every transmitting fiber and the inlet aperture of each and every receiving fiber of an individual catheter for all catheters within a population of catheters; and by making the size and shape of all the outlet apertures of all transmitting fibers generally uniform and the size and shape of the inlet apertures of all receiving fibers generally uniform in each catheter and from catheter to catheter and that the orientation of all transmitting fibers relative to all receiving fibers be similar.

18 Claims, 9 Drawing Figures

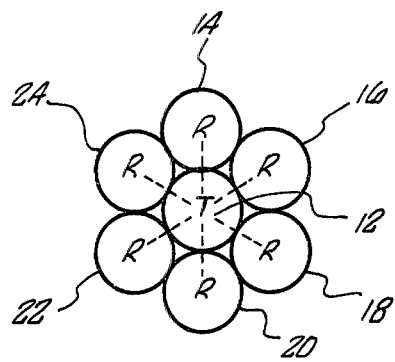
FIG_1_
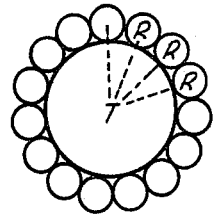
FIG_2_
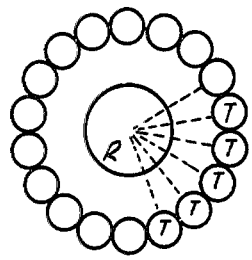
FIG_3_
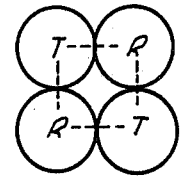
FIG_4_
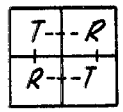
FIG_5_
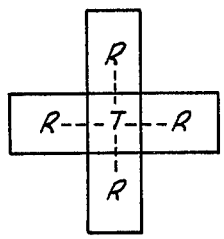
FIG_6_
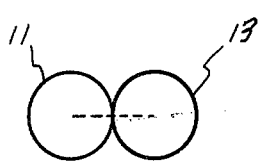
FIG_8_
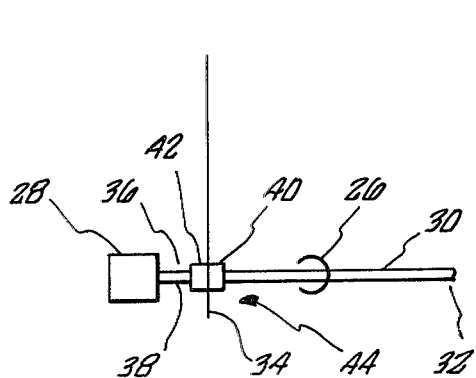
FIG_9_

OPTICAL CATHETERS AND METHOD FOR MAKING SAME

This is a continuation, of application Ser. No. 733,279, filed Oct. 18, 1976 now abandoned.

RELATED APPLICATIONS

The subject of this application is related to the subject matter of pending application Ser. No. 733,278 filed on Oct. 18, 1976 and entitled "Improved Catheter Oximeter Apparatus and Method " (now U.S. Pat. No. 4,114,604), and to the subject matter of application Ser. No. 733,280 filed on Oct. 18, 1976 and entitled "Sterilizable Disposable Optical Scattering Reference Medium" (now abandoned), the disclosures of which are incorporated herein by reference.

BACKGROUND OF THE INVENTION

Optical catheters for performing in-vivo spectrophotometric measurements in the blood stream or elsewhere within living organisms are well-known in the art. (See U.S. Pat. No. 3,847,483) These have most commonly been used for the performance of oximetry, i.e., measuring the relative amount of the total hemoglobin within the blood stream that is in the oxygenated form. While prior art optical catheters can be used successfully for performing oximetry, they have a shortcoming which is of major importance to the medical practioner in the care of critically-ill patients. The catheters of the prior art require that an individual calibration be performed for each and every individual catheter that is to be used, in order to obtain accurate oxygen saturation measurements.

To perform this calibration, commonly a sterile optical catheter is inserted through the wall of a blood vessel of interest and advanced so that its tip is at a position within the flowing blood stream where it is desired that oxygen saturation measurements be made. The patient is frequently given a particular gas mixture to breathe; commonly a mixture enriched in oxygen or depleted of oxygen, or two such mixtures sequentially, which causes the patient's blood to attain an oxygen saturation level in the regions of interest. Thus, as blood samples are withdrawn (most .commonly through an open lumen of the optical catheter) measurements are made of the relative light reflectances or transmissions at the catheter tip for the various optical wavelengths used by the catheter oximeter system.

The blood samples must then be taken to a separate instrument (for example, a transmissionspectrophotometer located in a central laboratory) where an independent measurement of the oxygen saturation of the one or more blood samples is made. The results of this independent measurement are then returned to the catheter oximeter at the patient's bedside, so that appropriate changes may be introduced into the catheter oximeter. These changes may include changes in bias levels and/or gains of various amplifiers in order to correct for the deviation between the initial oxygen saturation measurement made at the time of blood sampling and the oxygen saturation measurement independently determined by the separate instrument.

This requirement for individual calibration of catheters has obvious and important deficiencies. One such deficiency is the delay between the time of catheter placement and the time at which accurate measurements of oxygen saturation utilizing the optical catheter can be obtained. This delay deprives the physician of important information at a time when such information is often of the utmost importance in caring for the patient. For example, at the time of delivery of a newborn infant with severe respiratory distress because of prematurity, or severe Rh Hemolytic Disease or with other disorders, the resuscitation of these sick infants (who may weigh only two to three pounds) is frequently a precarious and difficult problem. This resuscitation must be instituted immediately upon birth and the various therapeutic manipulations completed within a very short time period. Unfortunately, the time required to perform calibration procedures on prior art optical catheters interferes with these catheters being used to furnish blood oxygen measurements during the course of resuscitation to guide the physician in the resuscitation procedure.

A second deficiency associated with calibrating the optical catheters of the prior art relates to the uncertainties associated with the resultant calibration. Changes in blood oxygen level occur continuously and often very rapidly, making it difficult to be certain that the blood sample and the oximeter readings are truly correlated. Further, during the process of blood sampling through the catheter tip, significant variations in flow profile of the red blood cells in the region where the optical measurements are being made may introduce errors into the optical measurements. In addition, the manipulations of the blood sample required to perform oxygen saturation measurement with an independent instrument can introduce errors in the calibration procedure.

It is therefore highly desirable to provide catheters which do not require individual calibration, so that each catheter of a whole population of catheters can be used to obtain blood oxygen measurement immediately upon introduction of the catheter into a blood vessel of interest.

SUMMARY OF THE INVENTION

In accordance with the present inventions, improved catheters which do not require individual calibration are made by using one or more transmitting optical fibers and one or more receiving optical fibers, having apertures at the distal ends thereof which are disposed to be immersed in blood under test, the apertures having centroids of cross sectional area which are equidistantly spaced between each and every transmitting fiber and each and every receiving fiber of each individual catheter and for all catheters within a population of catheters, and by making the size and shape of all the outlet apertures of all transmitting fibers generally uniform, and the size and shape of the inlet apertures of all receiving fibers generally uniform in each catheter and from catheter to catheter in a population of catheters, and that the orientation of all transmitting fibers relative to all receiving fibers be similar.

DESCRIPTION OF THE DRAWINGS

FIGS. 1 and 2 are sectional views of the distal ends of catheters according to the present invention in which a plurality of receiving optical fibers (R) are disposed continguous to the transmitting optical fiber (T) and in which the centroid of area of each receiving optical fiber (R) is equidistantly spaced from the centroid of area of the single transmitting optical fiber; and FIG. 3 is a sectional view of the distal end of another embodiment of a catheter according to the present invention in which each of the transmitting or receiving optical fibers is positioned remotely from a single receiving (or transmitting, respectively) optical fiber, with the centroid of area of each of the remotely-positioned optical fibers disposed equidistantly from the centroid of area of the single, centrally-located optical fiber; and FIGS. 4 and 5 are sectional views of the distal ends of still other embodiments of catheters according to the present invention in each of which the centroid of area of each of a pair of receiving optical fibers (R) is equidistantly disposed from the centroid of area of each of a pair of transmitting optical fibers (T); and FIG. 6 is a sectional view of the distal end of another embodiment of a catheter according to the present invention in which the centroid of area of each of a plurality of rectangular receiving optical fibers (R) is equidistantly disposed from the centroid of area of a single, square transmitting optical fiber (T); and FIG. 7 is a graph showing the distribution of light flux at different wavelengths and blood conditions as a function of distance from the centroid of area of a round transmitting optical fiber at the distal end of the catheter; and FIG. 8 is a sectional view of a single embodiment of a catheter according to the present invention in which a pair of substantially cylindrical optical fibers are contiguously disposed at the distal end of the catheter; and FIG. 9 is a plan view of the optical fibers of a catheter according to the present invention engaged with a photometric measuring device at an optically-coupled interface.

DESCRIPTION OF THE PREFERRED EMBODIMENT

Figure 1:
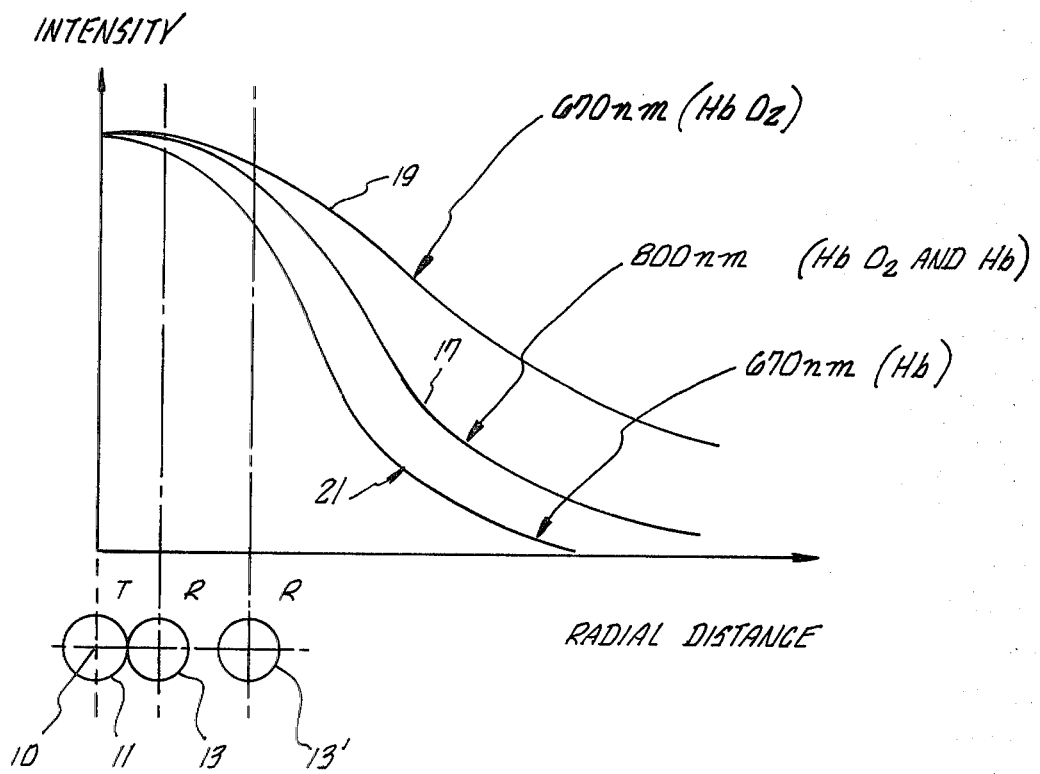

Referring now to FIGS. 1 through 6, there is shown in each figure the end sectional view of the optical fiber position at the distal ends of optical catheters according to the present invention. In these figures, there is at least one optical fiber designated with a "T" to indicate a fiber which transmits radiation to blood under test and the end sectional view of at least one optical fiber designated with the letter "R" to indicate a fiber which receives radiation from the blood under test. It should be understood that, with respect to FIGS. 1 through 6, the transmitting fibers and receiving fibers may be transposed in which case each "R" would represent an optical fiber which transmits radiation to blood under test and each letter "T" would indicate an optical fiber which receives radiation from the blood under test. Where more than one waveband of radiation is transmitted to the blood under test, there may be a number of transmitting fibers at least equal to the number of wavebands of radiation being transmitted to the blood under test; or alternately, and preferably, all wavebands of radiation used may be transmitted sequentially down each transmitting fiber.

Radiation that is transmitted down the transmitting fiber illuminates the blood, and the intensity of this radiation falls off with distance because of scattering and absorption. Some portion of that light which illuminates the blood is back-scattered by the red blood cells and is collected by receiving fibers which guide this collected light back to a measuring instrument (not shown) where the light intensity is measured by a photodetector element. It is the total light collected by the entire portion of each and every receiving fiber that is measured by the photodetector. To a usable approximation, for radiation of wavelengths in the optical portion of the electro-magnetic spectrum used, and for optical fibers having dimensions of the order of ten thousandths of an inch, the centroids of the areas of the apertures of the transmitting and receiving fibers substantially correspond with the centroids of the illuminating and the receiving light fluxes merging from and being collected by the apertures of the optical fibers. For circular fibers, as shown in FIGS. 1 through 4, the centroid of the cross-sectional area of each fiber is the center of the circle. However, fibers having apertures with cross-sectional shapes other than circular also have centroids of cross-section and can be used. For example, for fiber apertures having rectangular cross-sectional shape at the distal end, as shown in FIGS. 5 and 6, the centroid of such cross-section is located at the intersection of the diagonals through the corners thereof. Similarly, if the fiber apertures have a triangular cross-sectional shape (not shown), the centroids of such cross-sections are located at the intersection of the bi-sectors of the sides thereof. Of course, the fibers may have other more complex cross-sectional shapes at their apertures, and it should be understood that such apertures also have centroids of cross-section.

Referring now to FIG. 7, the graph portion illustrates the intensity of received light as a function of distance from the centroid of a transmitting fiber for two different wavelengths and two different conditions of oxygenation of blood under test.

Specifically, in Curve 17 the intensity (or light flux) measured at the 800 nanometer waveband is substantially the same for hemoglobin and oxy-hemoglobin and decays with distance away from the centroid 10 of the transmitting optical fiber 11. Curves 21 and 19 illustrate that the radiation intensity (or light flux) measured at the 670 nanometer waveband falls off with distance measured from the centroid 10 of the transmitting optical fiber 11 at a more rapid rate for reduced hemoglobin (Curve 21) than for oxyhemoglobin (Curve 19). From these curves it can be shown that the integral of light flux received by a receiving optical fiber 13 over the total cross-section area at a given wavelength will be the same for all equidistantly-spaced locations from the transmitting optical fiber 11. These curves also illustrate that for a receiving optical fiber 13' which is placed a greater distance from transmitting optical fiber 11 than receiving optical fiber 13, the integral of light flux received at a given wavelength will be less for optical fiber 13' than for optical fiber 13. Further, the light flux received by fiber 13' compared with the optical flux received by fiber 13 will be relatively different for different wavelengths, thereby introducing a wavelength-dependent aspect to the change in the optical properties of the catheter.

Returning now to FIG. 1, it can be seen that if light at all the optical wavebands used for the measurement is transmitted down the single optical fiber 12, the received light intensities of each waveband relative to each other waveband will be unchanged whether one receiving fiber 14 is used, or the entire array of receiving fibers 14 through 24 are used, or if some number of receivers between these two cases is selected, as long as the center-to-center spacing from the transmitting fiber to each of the receiving fibers 14 through 24 remains identical.

As a practical matter, individual fibers in a group of, say, receiving fibers may break or may have poorer or better optical transmittion properties than the average. As long as the center-to-center spacing between the transmitting and receiving fibers remains constant, the loss of one of a group of such receiving fibers (unless it is the only one) and the concomitant variation in the transmitting properties of such group of receiving fibers will not influence the relative light-intensities measured at the various wavelengths.

FIG. 4 illustrates an embodiment of the invention involving multiple transmitting and multiple receiving-optical fibers. In this embodiment, as long as the center-to-center spacing between all transmitting and all receiving-optical fibers remains constant, the relative light-intensities measured at the various wavelengths utilized will be unchanged, despite fiber breakage and variations in fiber transmissivity.

FIGS. 2 and 3 illustrate embodiments of the invention in which the transmitted optical fibers and the receiving optical fibers are not the same size. However, in these embodiments, it is only necessary that all of the transmitting optical fibers be identical in size to each other and all of the receiving optical fibers be identical in size to each other, and that the center-to-center spacing between each of the transmitting optical fibers and each of the associated receiving optical fibers remains constant.

FIGS. 5 and 6 illustrate other embodiments of the invention in which all of the fibers are not circular in shape. Rather, it is only necessary that the transmitting fibers be similar in size and shape, and that the receiving fibers be similar in size and shape and that the orientation of all transmitting fibers relative to all receiving fibers be similar to maintain the advantages noted above.

FIG. 3 illustrates another embodiment of the invention in which the transmitting and receiving fibers are not contiguous to each other. However, all of the operating advantages noted above may be retained by making the center-to-center spacing between each transmitting optical fiber and each receiving optical fiber substantially the same and by making the sizes and shapes of the transmitting optical fibers substantially the same within the group thereof and by making the sizes and shapes of the receiving optical fibers substantially the same within the group thereof.

FIG. 8 illustrates the simplest, most economic, and most readily manufacturable embodiment of an optical catheter according to the present invention. In this embodiment, a single transmitting optical fiber 11 and a single receiving optical fiber 13 of identical size are placed contiguous to each other. This configuration minimizes the amount of fiber material required, reduces the number of processes required to make the fibers, simplifies the sorting required of fibers, and readily assures the relationship between optical fibers discussed above.

Referring now to FIG. 9, the improved optical catheter 26 of the present invention typically operates in conjunction with a photometric measuring device 28 which furnishes one or more wavebands of light for transmission down the transmitting optical fiber or fibers 30 and which has a photodetector means for measuring the intensity of light collected by the receiving optical fiber or fibers 32. Thus, at the proximal end 34 of the present optical catheter, the optical fibers must be conveniently coupleable to such a measuring device 28. To produce reliable accurate photometric measurements, a repeatable stable optical relationship between the proximal ends 34 of the transmitting and receiving optical fibers 30, 32 of the catheter 26 and the corresponding optical channels 36 and 38 of such a measuring device 28 must be attained. While both the optical channels 36, 38 of such a measuring device and the proximal end surfaces or apertures 34 of the corresponding optical fibers 30, 32 of the catheter 28 are nominally flat and perpendicular to the axis of light transmission, certain variations in geometric normality can occur and these surfaces may be irregular and imperfect. If the coupling between the optical channels 36, 38 of such a measuring device and the proximal end surfaces of the optical fibers 30,32 is less than intimate, specular reflections will occur wherever an air/surface interface occurs, and this introduces undesirable extraneous light-intensity variations in the signals being measured by such measuring device. In addition, less than intimate optical coupling between the optical channels of such a measuring device and the proximal end surfaces of the corresponding optical fibers may produce optical interference patterns which are wavelength dependent and which therefore can produce spurious changes in the relative light-intensities measured at the various wavebands being used.

To avoid the error introduced by specular reflections and by interference patterns at the optical coupling interface 34 between a measuring device and the optical fibers 30,32, it is important that intimate surface contact be attained and maintained, even during use where patient motion and other extraneous factors may introduce undesirable forces which tend to misalign and disengage the optical coupling at this interface 34. In accordance with one embodiment of the present invention intimate contact between optical channels 36, 38 and optical fibers 30, 32 at interface 34 is attained and maintained by using a material in the optical fibers 30, 32 which is softer and more compliant than the material in the optical channels 36, 38 of the measuring device 28 with which they engage. In addition, the housing 40 for the optical fibers 30, 32 be made of a material that is softer and more compliant than the material of the housing 42 which surrounds the optical channels 36, 38. Further, to attain and maintain this intimate optical contact between the proximal ends 34 of the optical fibers 30, 32 and the optical channels 36, 38 of the measuring device 28, it is desirable to employ means to apply an axially-aligned force 44 to the optical catheter housing 40 which will establish an axial force at the mating surfaces between the proximal ends 34 of the optical fibers 30, 32 and the optical channels 36, 38. One suitable material to use in the optical fibers 30, 32 for interfacing with optical channels 36, 38 made of glass having the properties referred to above is styrene.

What is claimed is:

1. A catheter for photometric analysis of a fluid, said catheter comprising a plurality of transmitting and a plurality of receiving optical fibers; each said optical fiber for conducting radiant energy therethrough from an aperture at one end thereof to an aperture at the other end thereof; each aperture of each transmitting and each receiving optical fiber at the distal end thereof having a centroid of area; the centroid of the aperture of the distal end of each and every transmitting optical fiber being equidistant from the centroid of the aperture of the distal end of each and every receiving optical fiber.

2. The catheter of claim 1 wherein the apertures of each transmitting optical fiber at the distal ends thereof are of substantially a same size and shape and the apertures of each receiving optical fiber at the distal ends thereof are of substantially a same size and shape.

3. The catheter of claim 1, wherein said fluid is a spectrally-absorbing optically-scattering fluid.

4. The catheter of claim 1, wherein said fluid is human blood.

5. A catheter for photometric analysis of a fluid, said catheter comprising a plurality of transmitting and at least one receiving optical fibers; each said optical fiber for conducting radiant energy therethrough from an aperture at one end thereof to an aperture at the other end thereof; each aperture of each transmitting and each receiving optical fiber at the distal end thereof having a centroid of area; the centroid of the aperture of the distal end of each and every transmitting optical fiber being equidistant from the centroid of the aperture of the distal end of each and every receiving optical fiber.

6. The catheter of claim 5 wherein the apertures of each transmitting optical fiber at the distal ends thereof are of substantially a same size and shape and the aperture of each and every receiving optical fiber at the distal ends thereof are of substantially a same size and shape.

7. The catheter of claim 5, wherein said fluid is a spectrally absorbing optically scattering fluid.

8. The catheter of claim 5, wherein said fluid is human blood.

9. A catheter for photometric analysis of a fluid, said catheter comprising at least one transmitting and a plurality of receiving optical fibers; each said optical fiber for conducting radiant energy therethrough from an aperture at one end thereof to an aperture at the other end thereof; each aperture of each transmitting and each receiving optical fiber at the distal end thereof having a centroid of area; the centroid of the aperture of the distal end of each and every transmitting optical fiber being equidistant from the centroid of the aperture of the distal end of each and every receiving optical fiber.

10. The catheter of claim 9 wherein the apertures of each and every transmitting optical fiber at the distal ends thereof are of substantially a same size and shape and the apertures of each receiving optical fiber at the distal ends thereof are of substantially a same size and shape.

11. The catheter of claim 9, wherein said fluid is a spectrally absorbing optically scattering fluid.

12. The catheter of claim 9, wherein said fluid is human blood.

13. A method for performing photometric analysis of fluids by employing photometric analysis equipment in combination with a catheter selected from the group consisting of catheters having (1) at least one transmitting optical fiber and a plurality of receiving optical fibers, (2) a plurality of transmitting optical fibers and at least one receiving optical fiber, and (3) a plurality of transmitting and a plurality of receiving optical fibers, each said fiber being capable of conducting radiant energy therethrough from an aperture at one end thereof to an aperture at the other end thereof, each said aperture having a centroid of area, the method comprising:

selecting for use only those catheters in which the distance from the centroid of area of the aperture at the distal end of each end every transmitting optical fiber of each selected catheter to the centroid of area of the aperture at the distal end of each and every receiving optical fiber of each selected catheter is a constant; and, operating the photometric analysis equipment in combination with all said selected catheters in accordance with operating parameters established for at least one of said selected catheters;

whereby photometric analysis of fluids with any of said selected catheters may be accomplished without the individual calibration of each selected catheter.

14. The method of claim 13 wherein the fluid is a spectrally absorbing optically scattering fluid.

15. The method of claim 13 wherein the fluid is human blood.

16. The method for performing photometric analysis of fluids comprising steps of (a) conducting said analysis using photometric analysis equipment in combination with a population of a plural number of catheters, wherein each catheter within said population of catheters is a catheter within the group consisting of catheters having (1) at least one transmitting optical fiber and a plurality of receiving optical fibers, (2) a plurality of transmitting optical fibers and at least one receiving optical fiber, and (3) a plurality of transmitting and a plurality of receiving optical fibers, each said fiber being capable of conducting radiant energy therethrough from an aperture at one end thereof to an aperture at the other end thereof, each aperture of each transmitting and each receiving optical fiber at the distal end thereof having a centroid of area, said centroid of area of the aperture of each and every transmitting optical fiber being equidistant from said centroid of area of the aperture of each and every receiving optical fiber at the distal end of each and every catheter of said catheter population; and (b) operating the photometric analysis equipment in accordance with operating parameters established for at least one catheter in said population.

17. The method of claim 16 wherein the fluid is a spectrally absorbing optically scattering fluid.

18. The method of claim 16 wherein the fluid is human blood.

* * * * *